(12) United States Patent
Jiang

(10) Patent No.: US 9,394,511 B2
(45) Date of Patent: Jul. 19, 2016

(54) RAPID SINGLE CELL BASED PARALLEL BIOLOGICAL CELL SORTER

(76) Inventor: Wenbin Jiang, San Ramon, CA (US)

( * ) Notice: Subject to any disclaimer, the term of this patent is extended or adjusted under 35 U.S.C. 154(b) by 719 days.

(21) Appl. No.: 13/308,751

(22) Filed: Dec. 1, 2011

(65) Prior Publication Data

US 2012/0142018 A1    Jun. 7, 2012

Related U.S. Application Data

(60) Provisional application No. 61/419,873, filed on Dec. 5, 2010.

(51) Int. Cl.
*G01N 33/543* (2006.01)
*C12M 1/00* (2006.01)

(52) U.S. Cl.
CPC ..................... *C12M 47/04* (2013.01)

(58) Field of Classification Search
CPC ............... B01L 2200/0647; B01L 2300/0864; G01N 15/14; G01N 2015/149
USPC .......................................................... 436/526
See application file for complete search history.

(56) References Cited

U.S. PATENT DOCUMENTS

| 2008/0160622 A1* | 7/2008 | Su et al. ........................... 436/86 |
| 2008/0213821 A1* | 9/2008 | Liu et al. .......................... 435/39 |

* cited by examiner

*Primary Examiner* — Mark Shibuya
*Assistant Examiner* — Pensee Do
(74) *Attorney, Agent, or Firm* — Gary F. Witting

(57) ABSTRACT

A disposable rapid cell sorter comprises of microfluidic chip with electrodes and sorts biological cells of interest through magnetic field and electric field based on biological cell functional antibody bonded magnetic beads and luminescent labeling.

14 Claims, 6 Drawing Sheets

RAPID SINGLE CELL BASED PARALLEL BIOLOGICAL CELL SORTER

CROSS REFERENCE TO RELATED APPLICATIONS

This U.S. Non-Provisional Patent Application claims the benefit of U.S. Provisional Patent Application No. 61/419,873 entitled "Rapid Single Cell Based Parallel Biological Cell Sorter", filed on Dec. 5, 2010 by Wenbin Jiang.

BACKGROUND OF THE INVENTION

The present invention relates to cell sorter which can be used to analyze and sort cells of interest for bio-medical applications.

Embryonic stem cells possess the ability to remain undifferentiated and propagate indefinitely in culture while maintaining their normal karyotypes and pluripotency to differentiate into the derivatives of all three embryonic germ layers (i.e. endoderm; mesoderm and ectoderm), including such highly specialized cells as neurons, pancreatic and heart cells, etc. that do not normally regenerate in vivo. In vitro differentiation, which is required for therapeutic applications, remains a stochastic process that non-specifically generates all the three germ layers and their derivatives to varying degrees. It is therefore necessary to purify the cell lineage of interest for clinical use. Similarly, adult stem cells for therapeutic applications can be harvested from various tissues of the human body (e.g. bone marrow, adipose tissue, etc.), but the cells need to be isolated and purified for therapeutic applications. Although first used for hematopoietic reconstitution, stem cells are now central to major efforts in regenerative medicine across multiple organ systems, including but not limited to; vascular, myocardial and neuronal repair. Central to all therapeutic efforts that utilize pluripotential stem cells is the ability to rapidly identify and non-destructively isolate individual cells using a cost effective process.

Developing of a cell based screening assay often requires identification and isolation of particular cells from a mixture of various kinds of cells. Moreover, in order to obtain reproducible data on cells and their use in cell-based therapies, reliable and non-destructive purification of cells is essential. Multiple cell isolation and purification techniques are being used in stem cell arena. Currently, magnetic-activated cell separation (MACS) provides a parallel rapid method for cell purification. However, due to the limited specificity of single antibodies in this technique and the omni-present non-specific binding, the purity of cell purification is marginal. It is usually used as a pre-purification method. The cell by cell sorting method currently provides the highest purification rates because multiple signals can be used to increase specificity. Fluorescence activated cell sorters (FACS) using flow cytometry are widely used in research clinics for cell isolation and purification. In a typical flow cytometer (1,2), individual particles pass through an illumination zone, typically at a rate of some 10,000 cells per second, and appropriate detectors, gated electronically, measure the magnitude of a pulse representing the extent of light scattering or fluorescence from labeled antibodies. The FACS instrument combines two basic functions: cell analysis and cell sorting. Fluorescence from labeled antibodies bound to cell surface markers is analyzed on a cell by cell basis in the analysis portion. The cell population of interest is then further sorted into a separate port and accumulated by electrically deflecting the flow stream. The essential character of the flow cytometric approach is strictly quantitative. The large number of available fluorescent antibody tags makes flow cytometry a unique tool for cell analysis and sorting.

FIG. 1 shows the schematic diagram of a conventional flow cytometric cell sorting system 100. A cell 103 passes the interrogation zone 102, where it is excited by laser beam 105 and its light scattering and fluorescence is collected by lens 107 and received by detection system 109. Typically, the flow cell 103 is vibrated at some 10s of kHz to ensure that a uniform stream of droplets emerges from the end of the flow cell. The cell concentration is dilute enough so that the majority of droplets contain either zero or one cell. If a cell or droplet has been identified to be of interest, it is electrostatically charged by 108, causing the droplet to be deflected while passing a system of electrodes 111 and 112. The sorted cells 113 and 114 are collected by the collection tubes 115 and 116, respectively. Since the fluid with cells 103 is moving at a rate of 1 to 10 ms/droplet and the distance from the flow cell interrogation zone 102 to the deflector formed by the electrodes 111 and 112 is about 5 mm, the sorting decision needs to be made in less than 0.5 to 5 ms, allowing the sorting of some thousands of cells per second.

However, the rather bulky and complicated nature of the instrumentation as shown in FIG. 1 leads to fairly low adaptation rates in clinical labs. It is very difficult for a clinical lab to obtain appropriate approvals necessary to certify the cleanliness due to patient sample contamination in flow system for therapeutic applications. Current cytometer require careful and extensive cleaning procedures or exchanging of their sample handling components for this application, which requires a highly trained technician and can take many hours between running samples.

SUMMARY OF THE INVENTION

It is accordingly an object of the present invention to provide a cell sorting system which can solve the above problems in the prior art and can be made compact in size, high in the design flexibility, low in cost and high in reliability. It is also an object of the present invention to provide a cell sorting system to analyze cell function at individual cell basis and to sort cells in parallel based on cell functionality obtained individually.

In accordance with an aspect of the present invention, the above object is attained by providing a state-of-the-art disposable microfluidics-based cell sorting chip that eliminates the source contamination, which is critical for the required purity in stem cell research. Our design overcomes the speed issue due to cell by cell analyzing in microfluidic system. Instead of cell by cell serial analyzing and sorting, we invented a parallel single cell analyzing and sorting system for the needs of rapid cell analysis and sorting. The cell allows rapid parallel sorting relying upon CCD imaging, electric force capture and magnetic field release technologies. The iterative cost of this technology would be less than one tenth the cost of MACS technology, less than one tenth the iterative time of FACS technology and have increased mission/patient flexibility via both variable chip design parameters and secondary spectroscopic information available from the exciting laser.

DESCRIPTION OF THE PREFERRED EMBODIMENTS

The present invention will be explained with reference to the accompanying drawings, in which parts having the same reference numbers represent identical parts.

Figure 1:
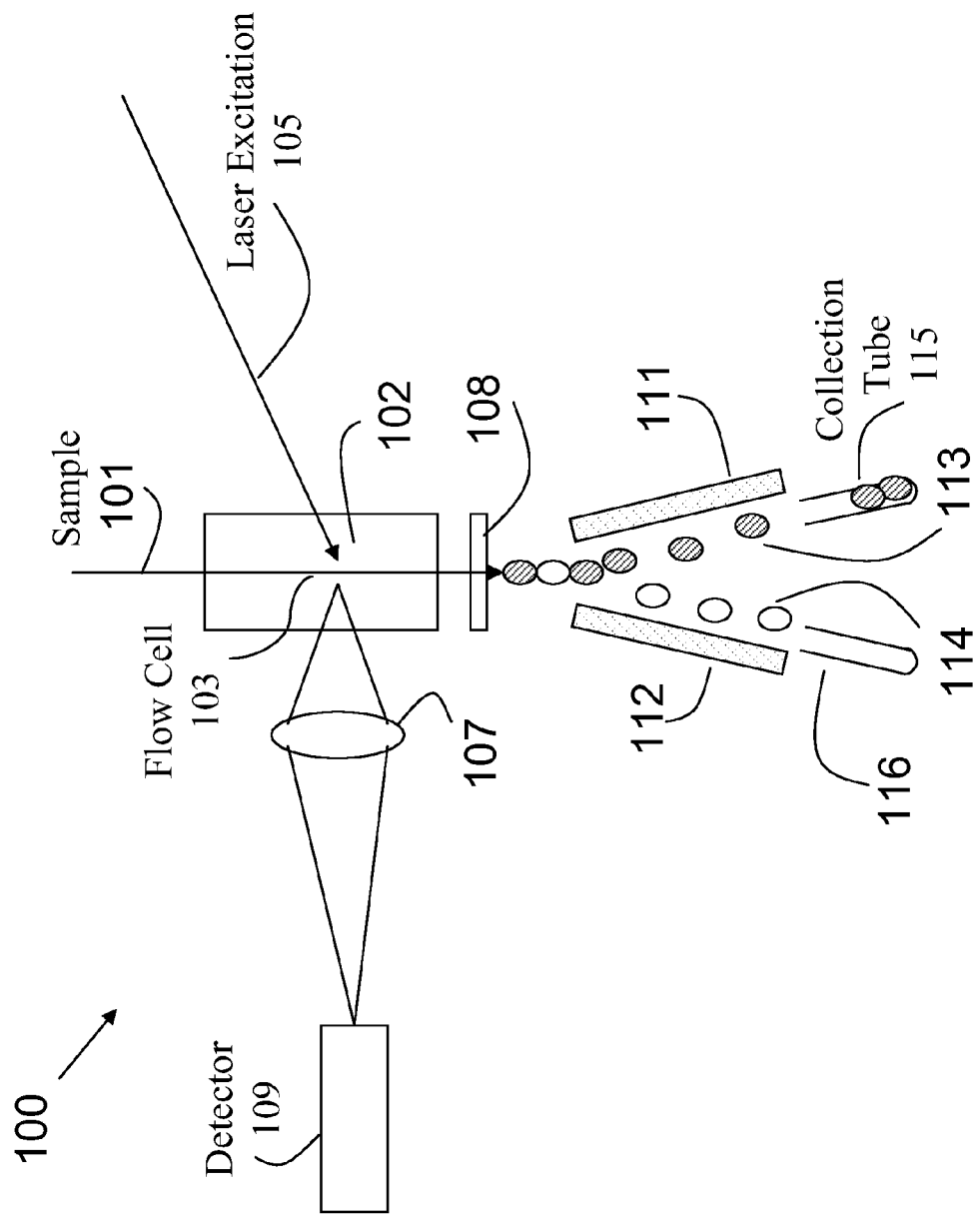
FIG. 1 is the configuration of a conventional cytometry for cell sorting.
Figure 2:
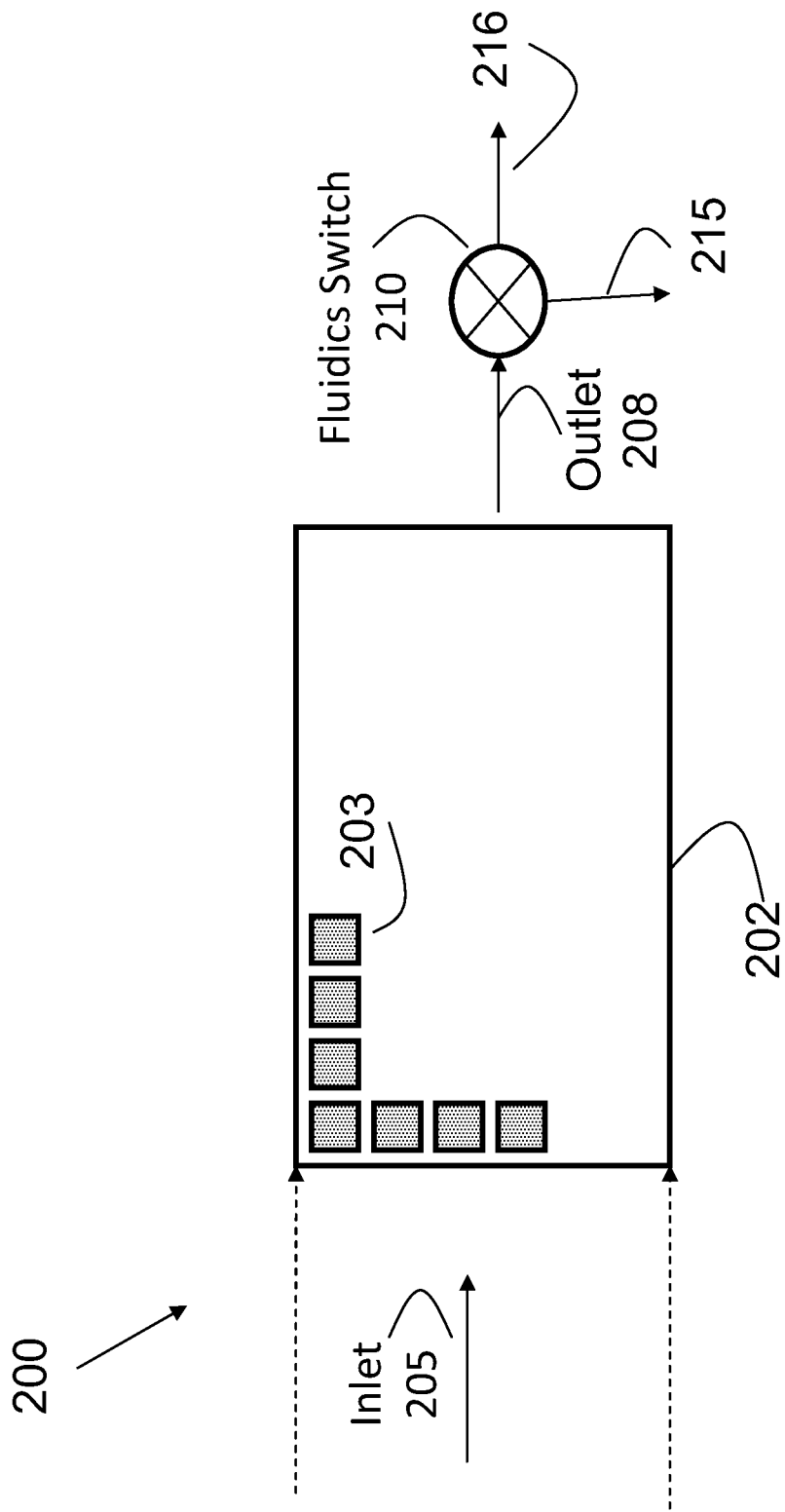
FIG. 2 is the schematics of a microfluidic cell sorter based on a present invention.

Turning now to FIG. 2, which is the schematic of a disposable parallel microfluidic cell sorter according to the current invention. The cell sorter 200 has a microfluidic chip 202 having a cavity, the cavity is transparent, flat and hollow, which is made of glass, molded plastics, gel, ceramics, silicon, GaN, sapphire, or a combination of materials with at least one side of the wall transparent. In a preferred embodiment, microfluidic chip 202 is a glass chamber of 1 to 1000 µm high, 0.1 to 10 mm long and 0.01 to 10 mm wide. Preferably, it is 10 to 300 µm high, 1 to 3 mm long and 1 to 3 mm wide. On one of the microfluidic chip walls, preferably the bottom side, there deposits the metal electrode array 203. The metal can be transparent ITO film, Au, Al, Cu, or any other conductive materials that may adhere to the chip materials. The electrodes may be enclosed by polymers. Each cell of the metal array 203 has a dimension of 0.1 to 100 µm and preferably 10 to 50 µm on each side of the cell. The spacing between the electrodes is 0.1 µm to 100 µm, and preferably 5 µm to 20 µm. On the wall opposite to the one with the metal electrode array 203, there may deposit a blank transparent metal electrode, such as ITO, for generating electric field between the electrode array 203 and the transparent metal electrode inside the microfluidic chip 202. Chip 202 has a fluid inlet 205 and a fluid outlet 208. A fluidic switch 210 switches fluid flow between port 215 and port 216.

Figure 3A:
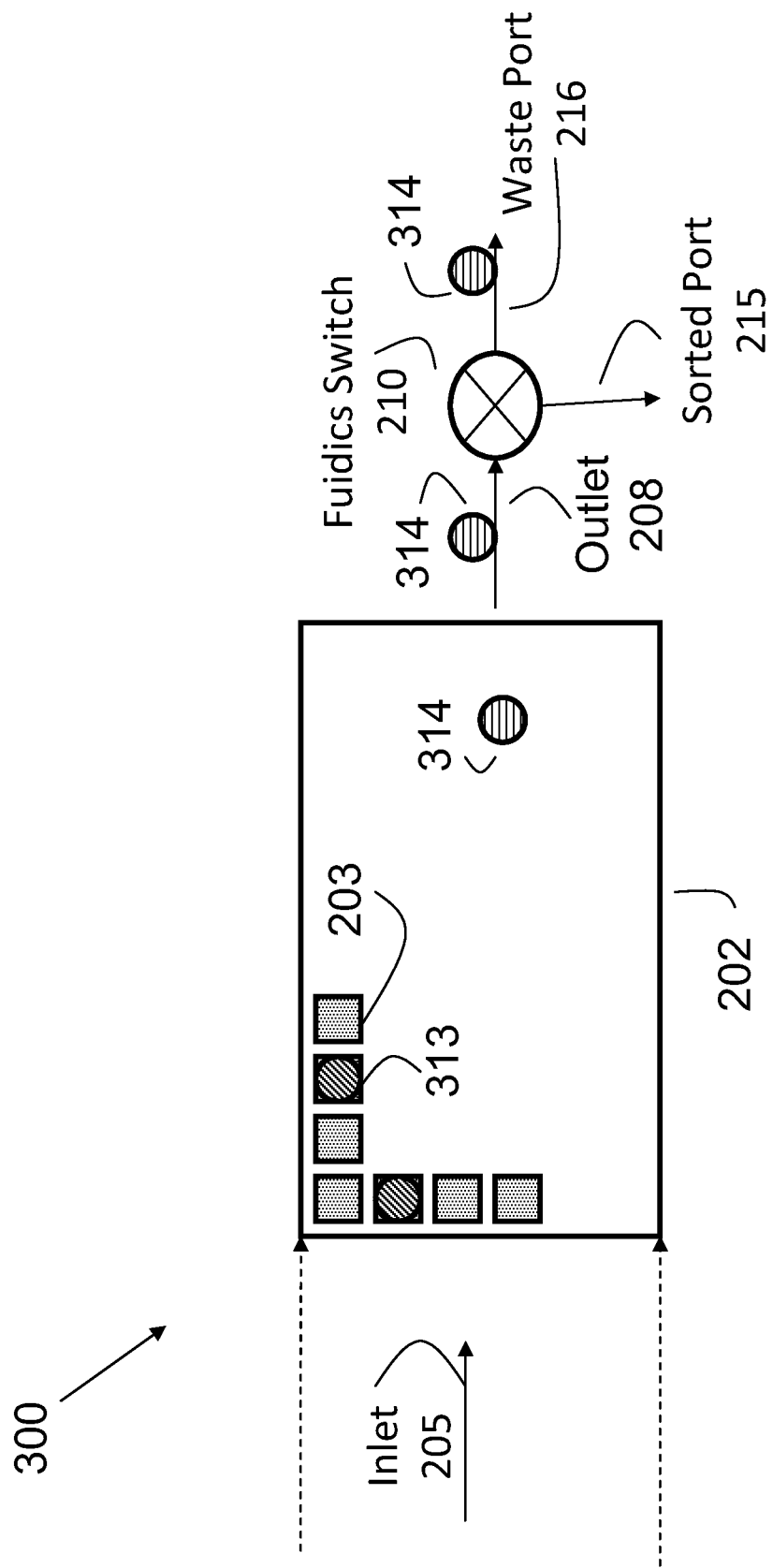
FIG. 3(a) shows the concept of a cell sorting process based on a present invention.
Figure 3B:
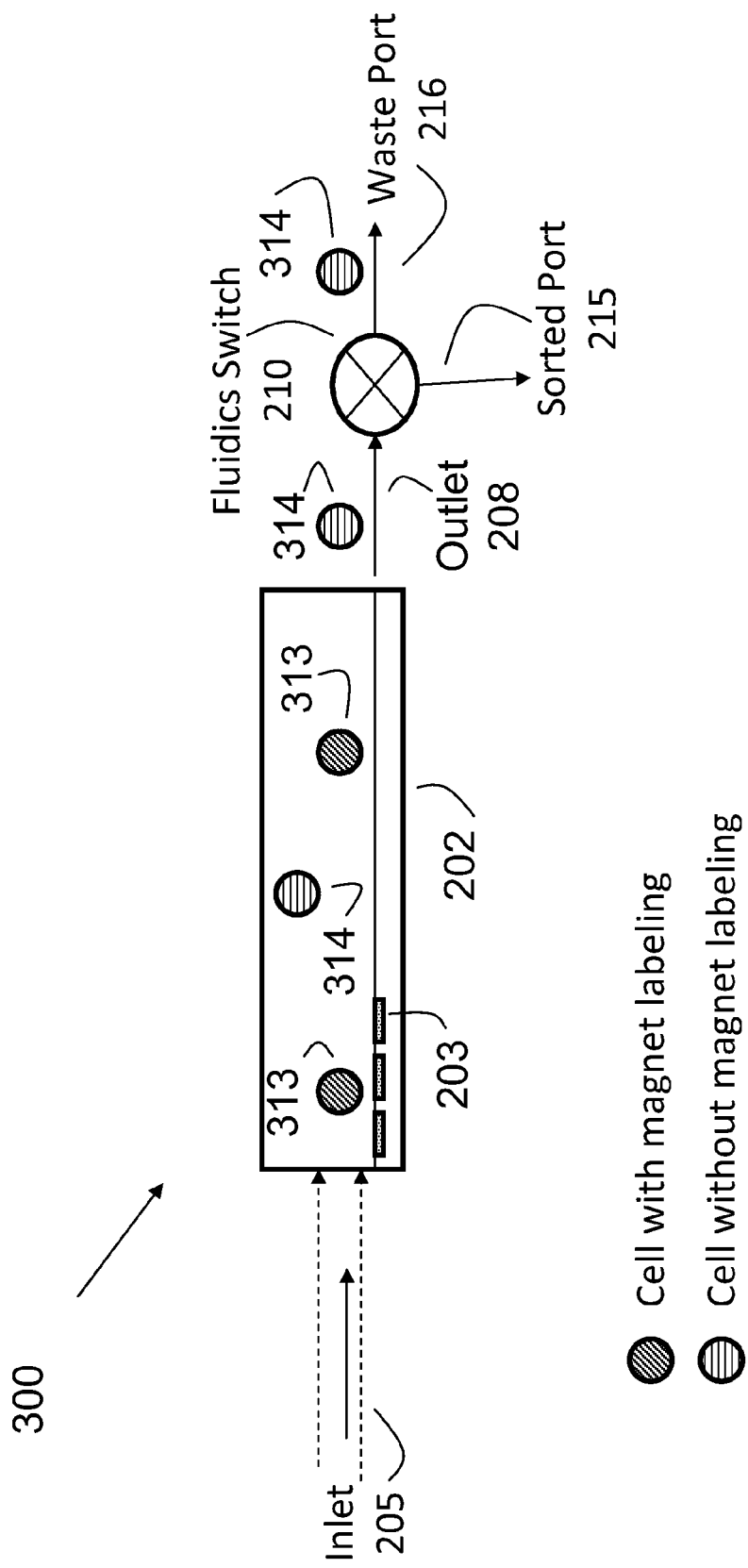
FIG. 3(b) shows a side view of a cell sorting process based on a present invention.
Figure 4:
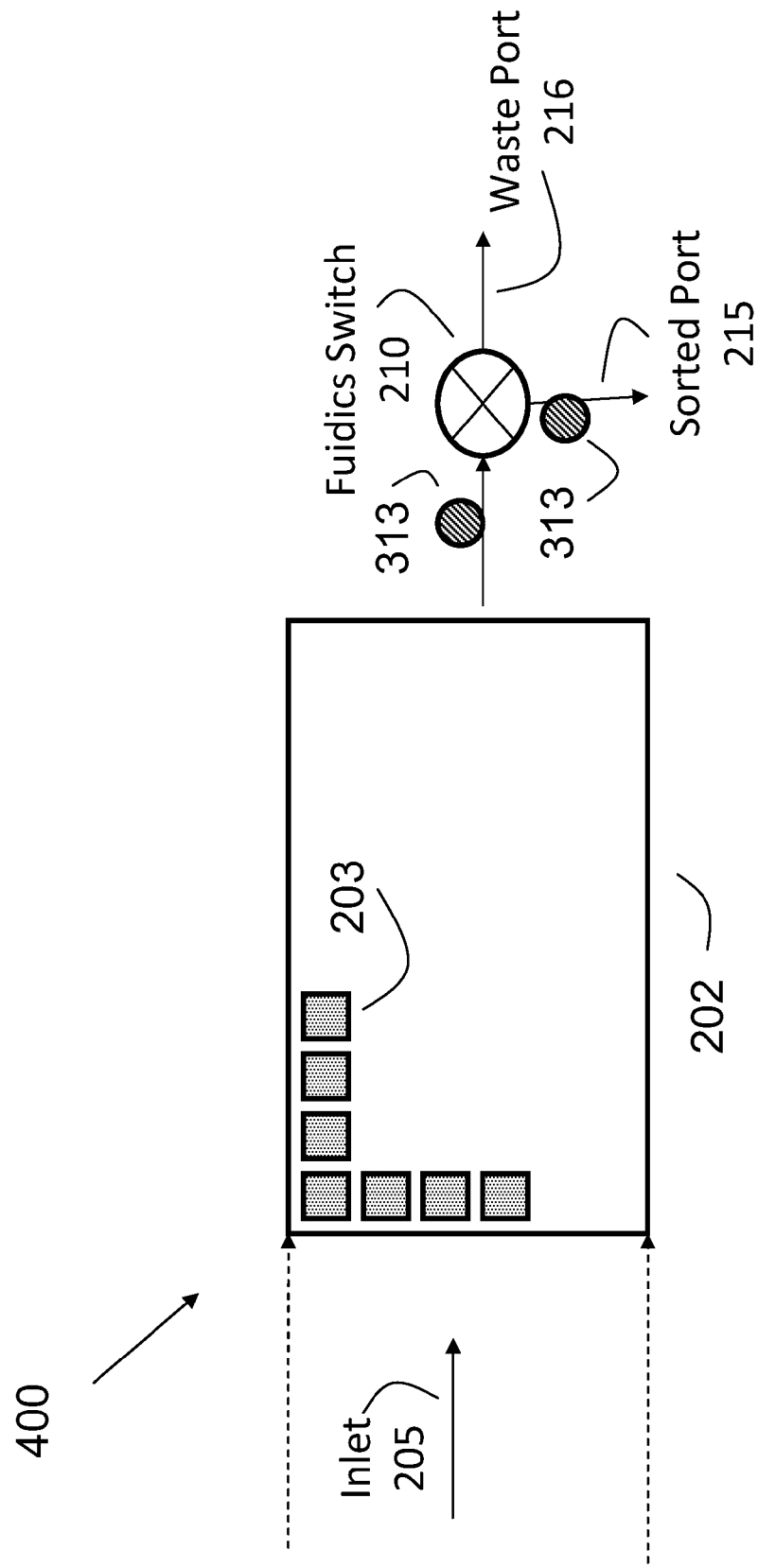
FIG. 4 shows the process of sorted cell collection based on a present invention.

FIG. 3(a) illustrates an operation principle of a disposable parallel cell sorter according to the present invention. A disposable parallel cell sorter 300 has a disposable microfluidic chip 202 having a cavity, the cavity is transparent, flat and hollow with fluid inlet 205 and fluid outlet 208. Biological cells of interest 313, such as CD45, CD4, CD8, etc, and irrelevant cells 314 are carried by fluid and enter the chip 202 through inlet 205. Cells 313 are normally pre-bonded to magnetized beads through antibody on the beads. The magnetized beads are naturally charged. The magnetized beads are normally less than 1 µm and preferably less than 0.1 µm in diameter. Cells 314 are not bonded to any magnetized beads. When cells 313 and 314 enter the microfluidic chip 202, magnetic field applied to the chip 202 which pulls cells 313 toward electrodes 203 and holds cells 313 in place inside the cavity, as shown by the side view in FIG. 3(b). Cells 313 are released when the magnetic field is no longer applied to chip 202. Cells 314 flow through outlet 208 and are collected by waste port 216 through fluid switch 210. Afterwards, cells of interest 313 are collected by sorted port 215 through fluid switch 210, as shown by system 400 in FIG. 4.

Figure 5:
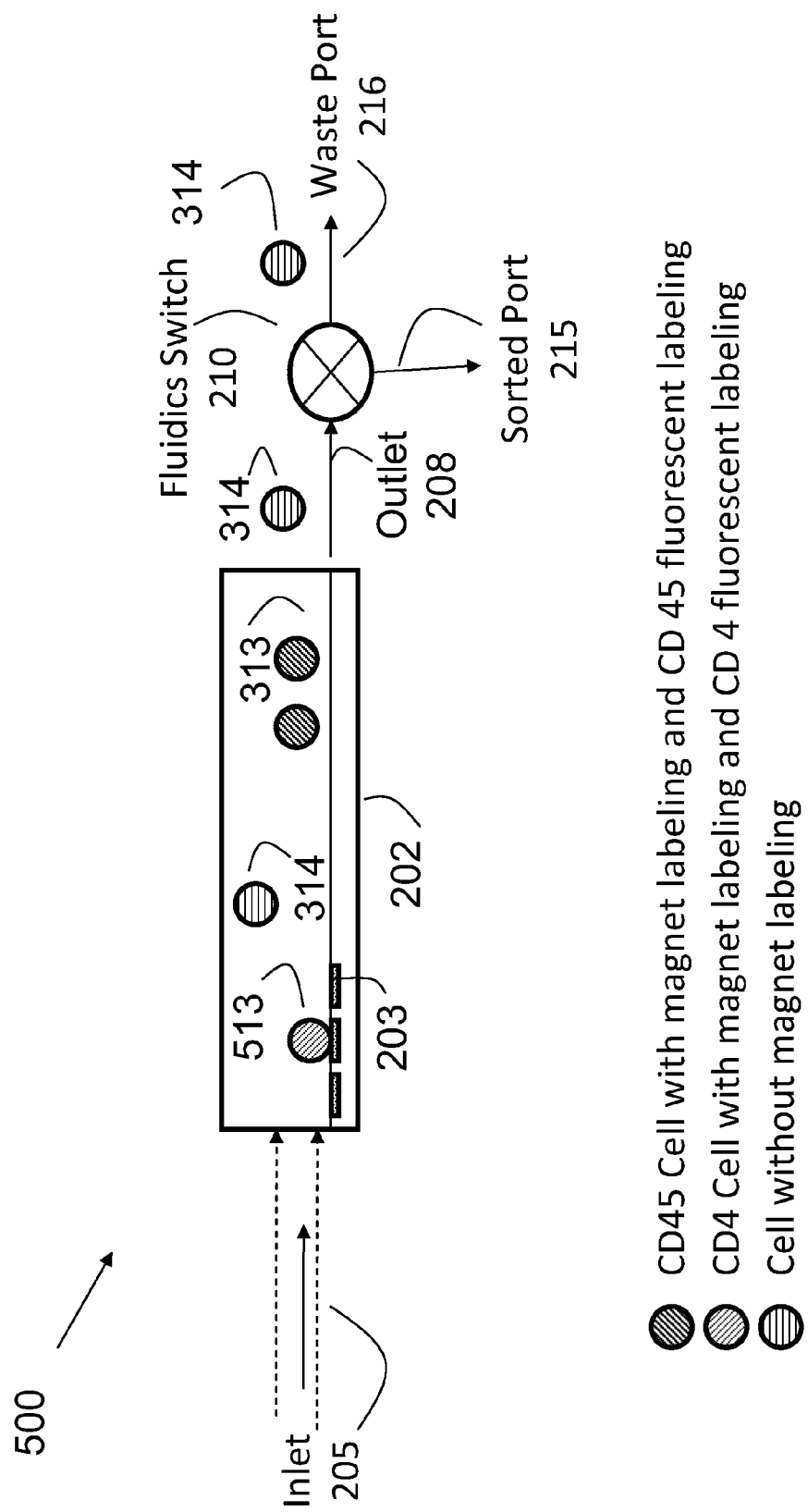
FIG. 5 shows the schematics of a cell sorter to sort cells using both magnetic field and electric field based on the present invention

When a subcategory of cells 313, such as CD4 or CD8 among CD45, designated as cells 513 in FIG. 5, must be sorted, Antibodies of the cells are pre-labeled with specific luminescence signature and attached to the cells of interest. When the cells to be sorted, including 313, 513 and 314 are loaded into the microfludic chip 202, magnetic field is applied to the chip 202 to pull cells 313 and 513 toward array electrodes 203, which is also an optical imaging plane of a detection system comprises of a lens or lenses and a detector or detector array, such as a CCD camera, PIN photodiode, APD, or PMT, which are not shown in the figure. Cells 313 and 513 lean against electrodes 202 randomly. An optical excitation system, such as a laser, is used to scan across the electrodes 202 to excite the luminescence of the cells. Cells 513 will generate specific luminescence and be detected. An electric field will be applied to the most adjacent cell of the electrode 202. As the magnetized beads of the cells are naturally charged, the electric field will force cells 513 to stay with electrode 203. This force is stronger than the magnetic force generated by the magnetic field, which pulls both cells 313 and 513 toward the optical imaging plane along the electrode 203. While a laser or LEDs can be used to excite the fluorescent antibody across the chip 202 electrodes 203, a spatially broadened laser beam can be used to excite all the cells within chip 202 simultaneously to increase the sorting rate. A two-dimensional detection system, such as a CCD camera, should be pre-calibrated to correlate the detection cells with the electrode cells 203, thus to synchronize the application of electric field on the cells that luminate.

When all the cells are characterized in chip 202, magnetic field is removed or flipped to allow cells 313 and 314 to exit outlet 208 and be collected into waste port 216. Sorted cells 513 remain staying with electrode 203 by the applied electric field.

Afterwards, there will be two paths to collect the sorted cells 513. The first approach is to turn off the electric field to allow cells 513 to exist outlet 208 and be collected into sorted port 215. The second approach is to keep cells 513 on the electrode 203 and new fluid is introduced into chip 202 to continue the sorting process. When electrode 203 is almost filled with sorted cells 513, chip 202 is taken off from the sorter as a sample for further characterization. Multiple photoluminescence labels can be applied to the correspondent antibodies to allow the sorting of multiple cells of interest in parallel using the same method described. The detection system should therefore be wavelength sensitive. A CCD camera with color filter is one example of a detection system that can be used to identify the wavelength of the luminescence. A memory map corresponding to the 2-D configuration of electrode 203 of the microfluidic chip is normally used to record the sorted cell position on chip 202 corresponding to the luminescence wavelength. There are multiple sorted cell collection ports connected to fluidic switch 210. When releasing sorted cells to the correspondent sorted cell collection port through fluidic switch 210, the 2-D electric field is withdrawn according to the memory map contents, thus, multiple biological cells can be sorted in parallel through multiple photoluminescence labeling.

To enhance the sorting efficiency and accuracy, magnetic field for sorting magnetically labeled cells can be generated by an array of micro-magnets, which can be controlled individually, thus increasing the cell sorting granularity. Also, photosensitive molecule or polymer may be introduced into the micro fluidic chip to pre-attach to one of the wall of the chip. When a cell of interest is detected, a light can be used to bond the cell to the chip wall through the photosensitive molecule or polymer, thus adding one more dimension to the cell sorting process for parallel cell sorting with multi-signatures based on single cell detection. The same optical method can be used to debond the optically bonded cells for sending the sorted cells to the correspondent sorted port through fluidic switch.

When each metal electrode cell dimension is kept at 20 μm×20 μm, and chip dimension is at 3 mm×3 mm, the total number of cells that can be sorted per micro fluidic chip is 22,500. Assuming the fluid dwelling time inside chip 202 is 1 second, the sorting rate of this cell sorter will be 22,500/sec. This cell sorting can be peformed after pre-richment of cells by magnetic beads. Therefore, the effective cell sorting rate can exceed 1 million cells per second with the combination of prerichment of cell of interests. This is equivalent to the current state of art cell sorting cytometry. Thus, the present invention has high practical effects. It function equally well for either positive or negative selection, providing yet another layer of mission/patient flexibility. Localization of the selection activity within a low cost chip is a practical, economical single use product that will eliminate the possibility of cross-contamination between iterations. It will be further possible to recycle chip material to decrease iterative costs and minimize environmental impact. In summary, this invention herein represents a more flexible technology that dramatically reduces the iterative time and cost of cell selection over currently available methodologies. This constellation of attributes is highly desirable for both clinical and research applications that require cell identification, enumeration, isolation/selection, or a combination thereof. This assures its application to a broad population of patients, clinical scenarios and research initiatives within Medical Oncology, Stem Cell Biology and Regenerative Medicine.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific feature of the invention described herein, and all statements of the scope of the invention which, as a matter of language, might be said to fall therebetween.

What is claimed is:

1. A rapid parallel single cell sorter comprising:
a microfluidic chip having a cavity, the cavity having a surface, the cavity is transparent, flat, and hollow, with an inlet for receiving a fluid containing relevant cells and irrelevant biological cells to be sorted, wherein the relevant biological cells are magnetically labeled with magnetic microbeads bonded to the relevant biological cells by antibodies, and flow into the transparent flat hollow cavity for holding the said fluid for cell sorting, and an outlet for releasing the said fluid containing the sorted cells;
a magnetic field generated to sort magnetically labeled biological cells and hold and release the said magnetically labeled biological cells in place in the cavity; and
a fluidic switch interfacing with the outlet to switch the fluid containing the sorted cells from the outlet toward one or more sorted cell collection ports.

2. The magnetic generator in claim 1 is an array of micromagnetics.

3. The rapid parallel cell sorter in claim 1 further comprises:
a layer of film on one of the flat hollow cavity surfaces of the said microfluidic chip;
a light source for the excitation of photoluminescence labeled biological cells; and
an optical detection system for capturing the photoluminescence from specific labeled biological cells.

4. The layer of film in claim 3 is an array of conductive electrodes for generating two-dimensionally addressable electric field extending into the microfluidic cavity according to the array pattern configuration.

5. The layer of film in claim 3 is a layer optic cross-linkable molecule or polymer for bonding or debinding labeled biological cells to the microfluidic surface though light illumination.

6. The said optic cross-linkable molecule or polymer in claim 5 includes but is not limited to DNA, RNA antibodies, peptides and proteins.

7. The optical detection system in claim 3 is a wavelength sensitive.

8. A rapid parallel single cell sorter comprising:
a microfluidic chip having a cavity with at least one surface being substantially flat and an inlet for receiving a fluid containing relevant cells and irrelevant biological cells to be sorted, the cavity being substantially transparent, flat, and hollow cavity for holding the said fluid for cell sorting, and an outlet for releasing the said fluid containing the sorted cells;
a fluidic switch interfacing with the outlet to switch fluid containing the sorted cells from the outlet toward one or more sorted cell collection ports;
a layer of film on one surface of the flat hollow cavity surfaced of the said microfluidic chip, the layer of film generates, a magnetic field extending into the fluid containing relevant cells and irrelevant biological cells in the flat hollow cavity to hold the relevant biological cells in place in the flat hollow cavity and to subsequently release the relevant biological cells;
a light source for the excitation of photoluminescence labeled biological cells; and
an optical detection system for capturing the photoluminescence from specific labeled biological cells.

9. The layer of film in claim 8 in an array of conductive electrodes for generating two-dimensionally addressable electrical field extending into the microfluidic cavity according to the array pattern configuration.

10. The layer of film in claim 8 is the layer of optic cross-linkable molecule or polymer for bonding or debonding labeled biological cells to the microfluidic surface through light illumination.

11. The said optic cross-linkable molecule or polymer in claim 10 includes but is not limited to DNA, RNA, antibodies, peptides and proteins.

12. The optical detection system in claim 8 is wavelength sensitive.

13. A rapid parallel single cell sorter comprising:
a microfluidic chip having a transparent hollow cavity with a surface and an inlet for receiving a fluid containing relevant and irrelevant biological cells to be sorted, the relevant biological cells are electromagnetically labeled biological cells that are bonded to antibodies containing electromagnetic micro-beads, and an outlet for releasing the said fluid containing the sorted cells;
an electromagnetic field generator capable of generating a field, wherein the field projects into the fluid of relevant and irrelevant biological cells to sort and hold in place electromagnetically labeled biological cells; and
a fluidic switch interfacing with the outlet to switch fluid containing the sorted cells from the outlet toward one or more sorted cell collection ports.

14. The said electromagnetic field generator in claim 13 sorts the said electrognetically labeled biological cells by selectively switch on/off the said electro magnetic field.

* * * * *